United States Patent [19]
Byce et al.

[11] Patent Number: 5,828,758
[45] Date of Patent: Oct. 27, 1998

[54] SYSTEM AND METHOD FOR MONITORING THE ORAL AND NASAL CAVITY

[76] Inventors: Michael L. Byce, 9878 W. Edna, Boise, Id. 83704; Joel E. Just, 4840 View Dr., Meridian, Id. 83642

[21] Appl. No.: 539,227

[22] Filed: Oct. 3, 1995

[51] Int. Cl.⁶ ................................................... A61F 1/20
[52] U.S. Cl. ............................................................. 381/70
[58] Field of Search ......................................... 381/61, 70

[56] References Cited

U.S. PATENT DOCUMENTS

| | | |
|---|---|---|
| 3,730,046 | 5/1973 | Spence . |
| 3,766,318 | 10/1973 | Webb .......................................... 179/1 |
| 3,878,748 | 4/1975 | Spence . |
| 3,914,550 | 10/1975 | Cardwell, Jr. ................................ 179/1 |
| 4,039,756 | 8/1977 | Burtschi ...................................... 179/1 |
| 4,502,150 | 2/1985 | Katz et al. ................................... 381/70 |
| 4,550,427 | 10/1985 | Katz et al. ................................... 381/70 |
| 4,612,664 | 9/1986 | Walsh et al. ................................. 381/70 |
| 4,672,673 | 6/1987 | Katz et al. ................................... 381/70 |
| 4,706,292 | 11/1987 | Torgeson .................................... 381/70 |
| 4,993,071 | 2/1991 | Griebel ....................................... 381/70 |
| 5,326,349 | 7/1994 | Baraff ......................................... 623/9 |
| 5,381,514 | 1/1995 | Aso et al. ................................ 395/2.73 |

*Primary Examiner*—Forester W. Isen
*Attorney, Agent, or Firm*—Ken J. Pedersen; Barbara S. Pedersen

[57] ABSTRACT

A system of the present invention includes a sound source for providing sound in the oral-nasal cavity, a microphone to receive sound modulated by the user's mouth, tongue, teeth, and lips as he or she speaks or attempts vocalization, and a circuit. The circuit, coupled to the microphone, generates an output simulating a male or female voice that conveys the modulation as intelligible speech. In one embodiment, the sound source provides subaudible sound. In another embodiment, the circuit includes a sampling circuit for digital signal processing. In yet another embodiment, the circuit with a transducer constitute the sound source for providing overtones and diagnostic waveforms in the mouth. According to a method of the present invention, a modulated sound signal with a first period is received from an oral-nasal cavity and used to form a second signal having a longer period for conveying the first signal's modulation at a lower fundamental frequency. By nonintrusive monitoring of the oral-nasal cavity, a simulated voice is provided without discomfort for the vocally disabled, including laryngectomees.

3 Claims, 6 Drawing Sheets

SYSTEM AND METHOD FOR MONITORING THE ORAL AND NASAL CAVITY

FIELD OF THE INVENTION

This invention relates to vocal communication and to monitoring an oral-nasal cavity to measure or to aid attempted vocalization.

BACKGROUND OF THE INVENTION

As an introduction to the problems solved by the present invention, consider conventional speech aids in common use by laryngectomees. One such aid requires the vocally disabled person to use one hand to continually press a vibrating solenoid against the soft tissues of the throat so that sound introduced into the mouth and nose can be modulated by moving the mouth, tongue, teeth, and lips. Another such aid is packaged as an upper denture so that use of the aid requires extraction of the vocally disabled person's upper teeth and the discomfort of operating an electronic sound source in the mouth.

These devices are cumbersome and often initially as well as subsequently painful to use. In social settings, operation of these devices can be unsettling to listeners due to the lack of natural tonal qualities in the simulated voice. In addition, use of some of these devices prevents two-hands-free mobility by the vocally disabled person. These deficiencies lead to decreased self esteem and additional detrimental psychological side effects for the vocally disabled person.

Some vocally disabled persons fall into disability due to a sudden inability to support more than a whisper or inabilities related to accident, partial paralysis, numbing, or sedation. For these people there is no opportunity for training in the use of a speech aid prior to the need for practical use as in calling for assistance or communicating with authorities, doctors, and loved ones.

In view of the problems described above and related problems that consequently become apparent to those skilled in the applicable arts, the need remains in the field of vocal communication for systems and methods for monitoring an oral-nasal cavity to measure or to aid attempted vocalization.

By "attempted vocalization" we include voluntary and involuntary reshaping of the oral-nasal cavity accompanied or unaccompanied by natural voice. The "oral-nasal cavity" generally describes the spaces surrounded by all tissues that naturally affect speech, including the mouth, nose, throat, ear canals, and sinus. Hence, the user of a system of the present invention is not necessarily vocally disabled, merely one whose oral-nasal cavity is to be monitored.

SUMMARY OF THE INVENTION

Accordingly, a system for monitoring a user's oral-nasal cavity in one embodiment of the present invention includes a sound source, a sensor, and a circuit. The sound source provides a first signal in the cavity. The sensor receives a second signal modulated by the cavity. The second signal is affected in part by the first signal and in part by the cavity. The sensor provides a monitor signal having a first modulation and a first period. The circuit, which is coupled to the sensor, determines a third signal. The third signal includes a second modulation responsive to the first modulation and includes a second period unequal to the first period.

According to a first aspect of such an embodiment, modulation by the oral-nasal cavity is monitored using a signal other than a signal broadcast to listeners. Simpler, less intrusive systems are feasible that need not preclude two-hands-free mobility by the user.

According to another aspect, the oral-nasal cavity is filled with sound without irritating soft tissues which may be in the process of healing when monitoring attempted vocalization is needed.

According to yet another aspect, by determining the second modulation and the second period with a circuit, these signal characteristics are manipulated electronically to match the user's voice prior to the onset of vocal disability, thereby minimizing the lack of tonal quality, reducing the possibility of degraded self esteem, and avoiding consequential psychological side effects.

In another embodiment of the present invention, a system for monitoring the oral-nasal cavity includes a circuit. In operation, the circuit receives a monitor signal from a sensor, such as a microphone. Sound from the cavity is induced by a transducer, such as a speaker. The result of modulation as received by the sensor is a monitor signal having a period. In response to the monitor signal, the circuit provides an output signal that conveys the modulation at a period unequal to the period of the monitor signal.

According to an aspect of such an embodiment, a sensor and transducer are packaged separate from the circuit to permit location in or near the oral-nasal cavity without requiring extraction of teeth, irritation of soft tissues, or adding to the initial or subsequent discomfort of the user. Consequently, the design of the circuit is less constrained and less expensive, more sophisticated, and more reliable systems result.

According to another aspect of such an embodiment, telemetric coupling of the sensor, transducer, and circuit may be used to further enhance user mobility.

The present invention may be practiced according to a method in one embodiment which includes the steps of receiving a first modulated sound signal and providing a second modulated signal. The first signal, from the user's oral-nasal cavity, has a first period and a first modulation. The second signal has a second period unequal to the first period and has a second modulation responsive to the first modulation.

According to a first aspect of such a method, neither step requires action by the user so monitoring may continue whether the user is fully conscious or not.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims.

A person having ordinary skill in the art will recognize where portions of a diagram have been expanded to improve the clarity of the presentation.

In each functional block diagram, a broad arrow symbolically represents a group of signals that together signify a binary code. For example, a group of address lines is represented by a broad arrow because a binary address is signified by the signals taken together at an instant in time. A group of signals having no binary coded relationship is shown as a single line with an arrow. A single line between functional blocks represents one or more signals. Signals that appear on several figures and have the same mnemonic are coupled together by direct connection or by additional devices.

In each timing diagram the vertical axis represents an analog voltage or current conveying modulation and the horizontal axis represents time. Units of measure on the vertical axes vary according to implementation details familiar to those of ordinary skill. The scale of the horizontal axes of all waveforms is the same for clarity, though the waveforms themselves are not necessarily synchronized.

DETAILED DESCRIPTION OF THE INVENTION

Figure 1:
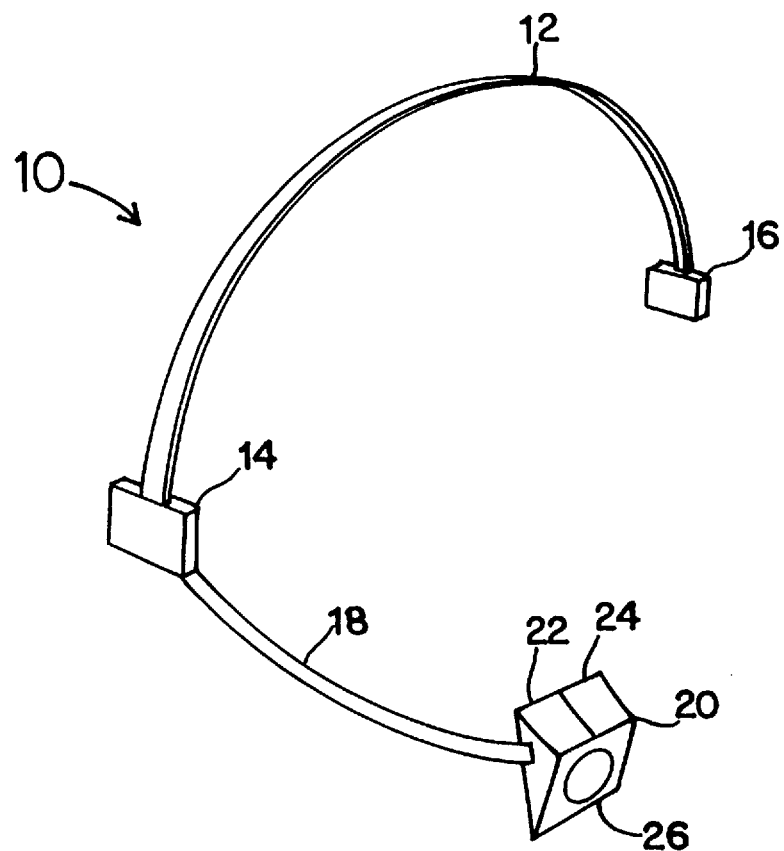
FIG. 1 is a perspective view of a headset according to an embodiment of the present invention.

FIG. 1 is a perspective view of a headset according to an embodiment of the present invention. Headset 10 includes headband 12, retaining pads 14 and 16, boom 18, and mouthpiece 20. Mouthpiece 20 includes transducer 22, sensor 24, and speaker 26.

Headset 10 is designed to fit comfortably over the head of the user whose oral-nasal cavity is to be monitored. Retaining pads 14 and 16 rest behind the user's ears, preventing movement of headband 12 and maintaining the position and orientation of mouthpiece 20 in relation to the cavity. Retaining pads are constructed of rubber or plastic materials for light weight, durability, and protection from moisture. Retaining pads 14 and 16 respectively enclose one or more batteries, not shown. Batteries are wired to mouthpiece 20 via wiring within boom 18. Operation of the system shown in FIG. 1 is best understood with reference to FIG. 2.

Figure 2:
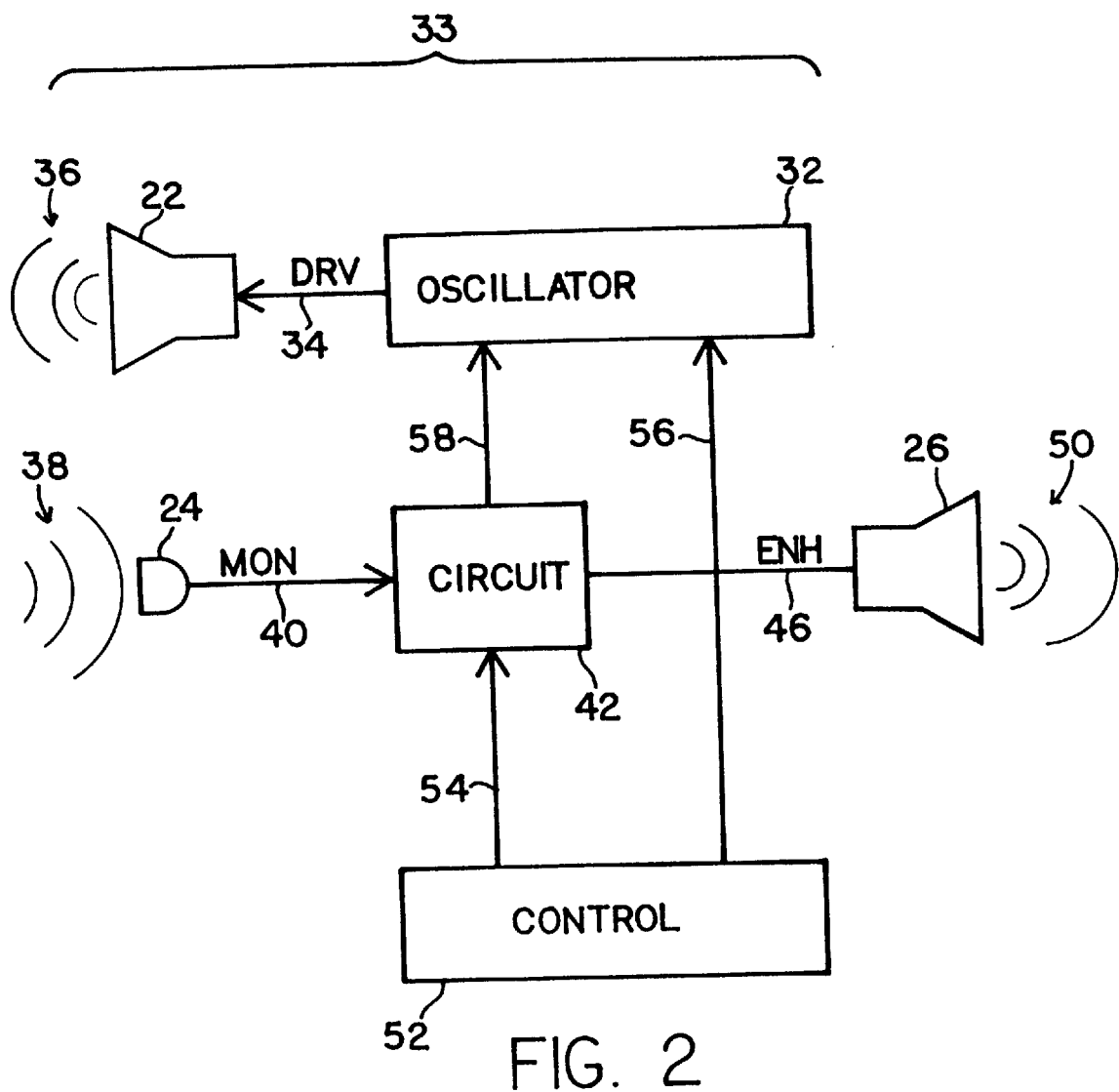
FIG. 2 is a block diagram of the embodiment shown in FIG. 1.

FIG. 2 is a block diagram of the embodiment shown in FIG. 1. Oscillator 32 generates drive signal DRV on line 34 to transducer 22. Transducer 22 emits sound signal 36 which is directed toward the user's oral-nasal cavity by boom 18 shown in FIG. 1. The cavity re-radiates sound signal 38 which includes part of the spectral energy of sound signal 36 as amplified and attenuated by the nonlinearities and resonances of the cavity. The distribution of spectral energy in signal 38 is herein called a modulation, and includes the spectral energy of the user's voice and consonant sounds, if any. As the user moves his or her mouth, tongue, teeth, and lips, the nonlinear and resonant characteristics of the cavity change. Therefore, the modulation of sound signal 38 conveys information about the cavity with or without the user's voice.

Oscillator 32 and transducer 22 cooperate as sound source 33 for sound signal 36, i.e. means for generating a signal having an audible frequency component. In general, an audible frequency component has a frequency within the range from 20 Hz to 20 KHz. Signal DRV on line 34 is electromagnetic having an audible frequency component. Transducer 22 provides means for radiating these frequency components as sound.

In an embodiment preferred for simplicity, sound source 33 is not coupled to circuit 42. Signal DRV has one frequency component so that transducer 22 emits a pure tone.

In another embodiment, oscillator 32 is omitted and transducer 22 and circuit 42 cooperate as a sound source. In such an embodiment, circuit 42 provides signal DRV having audible frequencies by digital techniques including waveform generation and filtering known in the art.

In yet another embodiment, oscillator 32 and sensor 24 are omitted. Transducer 22 is coupled to circuit 42 for two modes of operation. In a first mode at a first instant of time, transducer 22 radiates signal 36 in response to signal DRV on line 34 provided by circuit 42. In a second mode at a time following the first time, transducer 22 receives signal 38 and provides signal MON on line 34 to circuit 42. Such an embodiment is preferred for minimum components and maximum reliance on the flexibility and reliability of digital circuit techniques used to realize circuit 42.

In variations of any of the above embodiments, sound source 33 generates signal DRV with multiple frequency components, with swept frequency components, and with harmonic frequency components for increasing the accuracy of monitoring an oral-nasal cavity in various user situations.

Signal 36 in a preferred embodiment is subaudible. A sound signal is subaudible by virtue of a lack of sound energy at audible frequencies sufficient to be identified over background sounds. For instance, when sound signal 36 is subaudible, the average experienced user with average hearing ability in a busy conversational situation is not irritated by sound signal 36 when present in his or her oral-nasal cavity. As another example, sound signal 36 is subaudible when its sound level is at least about 20 dBA (A-scale weighting) below the combined noise and conversation levels as measured three feet from the user.

Sound signal 38 is received by sensor 24 which converts sound energy into electromagnetic monitor signal MON on line 40. Because signal 38 is sound, signal MON has a period. The modulation of sound signal 38 is reproduced on signal MON according to the transfer function and directional sensitivity of sensor 24. In a preferred embodiment, sensor 24 is an omnidirectional microphone with flat frequency response over a wide band, for example, approximately 20 Hz to 15 KHz. Sensor 24 provides means for detecting sound energy and includes a sound pick up device, microphone, pressure sensor, differential pressure sensor, resonant device, combinations thereof and equivalents.

Circuit 42 receives signal MON on line 40, detects the modulation thereon, and applies the modulation to enhanced signal ENH on line 46. For manual monitoring purposes, signal ENH, in the embodiment shown in FIG. 2, drives speaker 26 to produce simulated speech sound signal 50 at conversational volume. Speech sound signal 50 in one embodiment includes audible frequency components that are out of phase with signals 36 and 38 to reduce the sound level of signals 36 and 38 outside the region local to sensor 24.

Speaker 26 is omitted in an alternate embodiment that monitors for purposes including, for example, instrumentation, analysis, emergency communication, transcription, robotics, and control. In such an embodiment, signal sources (not shown) and actuators (not shown) cooperate in response to signal 38. These features permit, for example, reliable "vocal" control of machinery in an environment that is too noisy for machine control by speech at normal volume.

To create simulated speech that approximately matches the original voice of the user, recordings of the user's voice prior to the onset of disability are made and analyzed for frequency patterns. These frequency patterns are simulated by weighted frequency component generation in oscillator 32 and circuit 42 as directed by control 52. Control 52 is coupled for conveying parameters to circuit 42 by line 54 and to oscillator 32 by line 56. Circuit 42 is coupled to oscillator 32 by line 58 for controlling oscillator operation in part in response to parameters received on line 54.

Control 52 includes electromechanical input devices such as switches, variable resistors, joy sticks, touch sensitive devices, and the like, for manual control inputs from the user. Manual control inputs allow the user to affect the intonation, volume, vibrato, reverberation, tremolo, randomization, attack, and decay functions well known in the music and speech simulator arts. Manual control inputs also initiate consonant sounds discussed below.

In a preferred embodiment that includes all elements shown in FIG. 2, control 52 is packaged for handheld use. In such an embodiment, lines 54 and 56 are implemented by cabling to mouthpiece 20 or by conventional telemetry to mouthpiece 20. In the latter case mouthpiece 20 additionally includes conventional compatible receiver or transponder circuits.

In an alternate simplified embodiment of the invention, control 52 is omitted. In such an embodiment, control functions, for example as discussed above, are implemented in circuit 42 as settings by, analog component selection, jumpers, switching, and/or data storage devices. This simplified embodiment is preferred for lower cost and higher reliability. In a machine control application, monitoring attempted vocalization of vowels is sufficient to distinguish simple terms such as "start," "slow," "fast," "stop," "right," "left," and "help."

In another embodiment, control 52 includes a conventional angular position sensor (not shown) mounted for example in either mouthpiece 20, boom 18, or pads 14 or 16 for providing a control signal to circuit 42 on line 54. In operation, for example, the user by nodding his or her head up or down directs circuit 42 to decrease or increase, respectively, the period of sound signal 50. As another example, the user distinguishes between related consonant sounds such as 'f' and 'v' by changing the position of the angular position sensor.

Although shown as a headset in FIG. 1, one of ordinary skill will realize that all of the functions described for headsets can be equivalently embodied in a hand held unit similar in shape to a conventional hand held microphone. In such an embodiment, the hand held unit includes an integrated circuit at one end and a speaker at the opposite end. The integrated circuit includes conventional integrated instrumentation for performing the functions described for transducer 22, sensor 24, and the above mentioned angular position sensor. In addition, the integrated circuit performs the functions described for oscillator 32, circuit 42, and control 52 using digital signal processing techniques, described below.

Returning to the embodiment shown in FIG. 2, the structure and operation of circuit 42 will be better understood with reference to a signal timing diagram, functional block diagram, and flow charts, discussed below.

Figure 3:
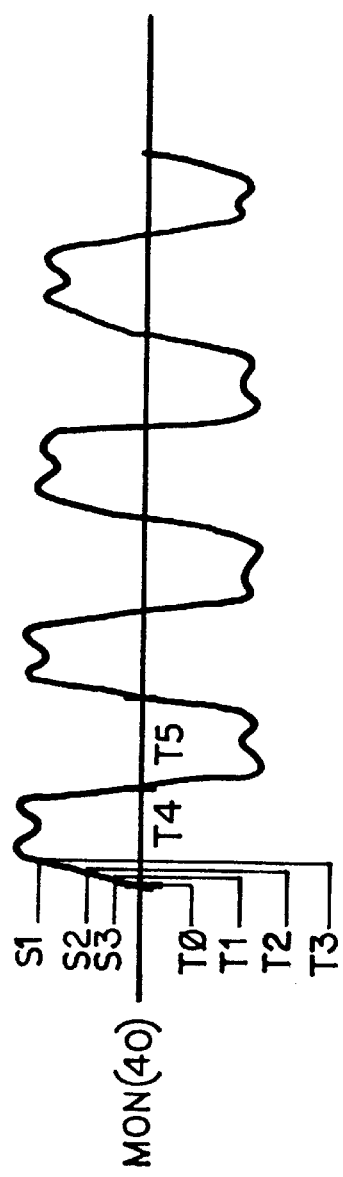
FIG. 3 is a timing diagram of signals identified in FIG. 1.
Figure 3:
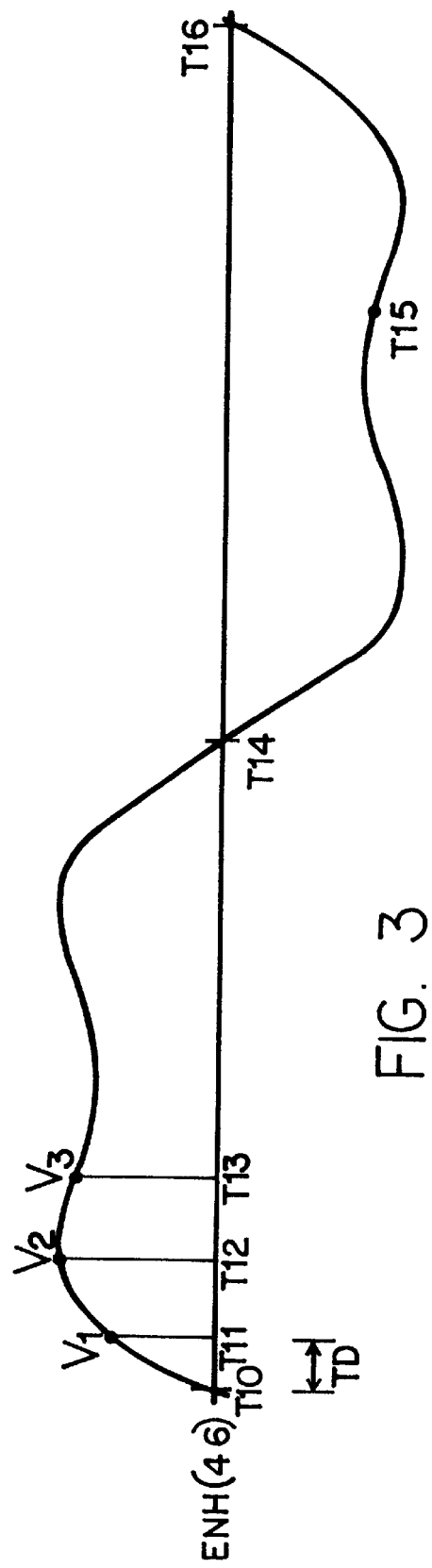

FIG. 3 is a timing diagram of signals identified in FIG. 2. Signal MON on line 40 has a period, measured for example from time T0 to time T5. The modulation, i.e. the deviation of signal MON from a single frequency sinusoid, is arbitrarily shown for purposes of illustration; however the rough similarity between the modulation of signal MON and the modulation of signal ENH on line 46 illustrates a basic function of circuit 42. Signal ENH has a period measured, for example from time T10 to time T16, approximately 8 times longer than the period of signal MON. In a preferred embodiment, signal DRV is a pure tone having a fundamental frequency approximately between 1 KHz and 2 KHz. Hence, the period of signal MON is correspondingly 1 millisecond to 0.5 millisecond respectively. This period is satisfactory for monitoring attempted vocalization, however, few listeners would prefer to listen to a speaker having such a high pitched simulated voice. Therefore, signal ENH is determined by circuit 42 with a period of about 10 times the period of signal MON to simulate a low male voice or about 8 times to simulate the higher pitched natural voices of women and children.

Circuit 42 includes means for remodulating. Remodulating, as described for example with reference to FIG. 3, functionally includes the detection of modulation on signal MON and the application of that modulation on signal ENH at a longer period. Such means, in one embodiment includes analog detection, discrimination, demodulation, filtering, modulation, and shaping circuits, individually known in the art. In an alternate and equivalent embodiment, means for remodulation includes digital circuitry in addition to, or in place of, some or all of the analog circuitry described above. A fully digital embodiment is better understood with reference to a block diagram.

Figure 4:
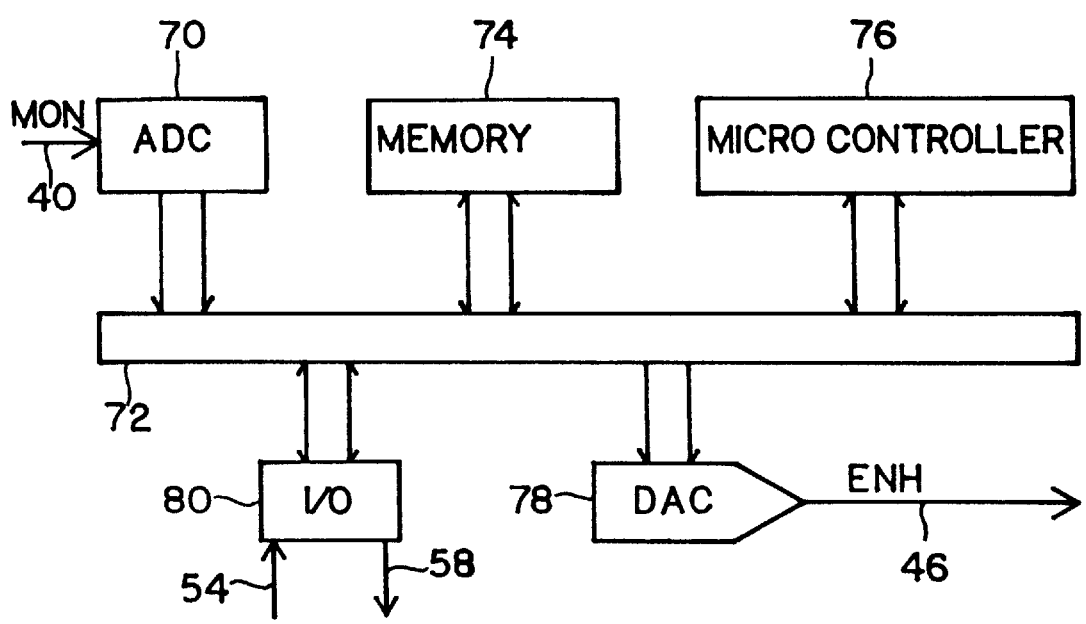
FIG. 4 is a block diagram of an embodiment of circuit 42 identified in FIG. 2.

FIG. 4 is a block diagram of an embodiment of circuit 42 identified in FIG. 2. Signal 40 is received by analog to digital converter (ADC) 70 via line 40 and is sampled under the direction of microcontroller 76 by conventional control signals, not shown. Microcontroller 76 receives these samples on bus 72 and stores them in memory 74.

Memory 74 provides microcontroller 76 with program steps to execute, provides storage space for program constants and control settings, and provides scratch pad memory for calculations. For these functions, memory 74 includes conventional read only, non-volatile, and dynamic memory circuits.

The program steps stored in memory 74 direct microcontroller 76 to form a series of values in an array in memory 76. These values are then supplied to digital to analog converter (DAC) 78 via bus 72. DAC 78 generates signal ENH on line 46 under the direction of conventional control signals from microcontroller 76, not shown.

Microcontroller 76 also receives input signals and directs output signals via input output block (I/O) 80. These inputs and outputs include control signals on lines 54 and 58 identified and described with reference to FIG. 2.

Analog to digital converter 70 includes a sampling circuit for capturing a portion of the amplitude of signal MON and holding it for the duration of a conversion. In an alternate embodiment, I/O block 80 and a sample and hold circuit, not shown, cooperate as a sampling circuit and ADC 70 is omitted. In such an embodiment, signal MON is input to I/O block 80 and the hardware functions of ADC 70 are performed by conventional software stored in memory 74 and executed by microcontroller 76.

In yet another alternate and equivalent embodiment, DAC 78 is omitted and the functions of DAC 78 are performed by microcontroller 76, I/O block 80, and conventional software stored in memory 74.

In a preferred embodiment, all functions shown on FIG. 4 are implemented with a conventional digital signal processor (DSP) integrated circuit. In an alternate embodiment, the DSP is used for additional functions including signal conditioning applied to signal MON and digital filtering applied to signal ENH. Specialized and sophisticated implementations of these functions for the purposes of enhancing monitor accuracy or more nearly simulating natural speech are individually within the ordinary skill of digital signal processing hardware and software designers familiar with audio cavities, music, and speech synthesis.

Figure 5:
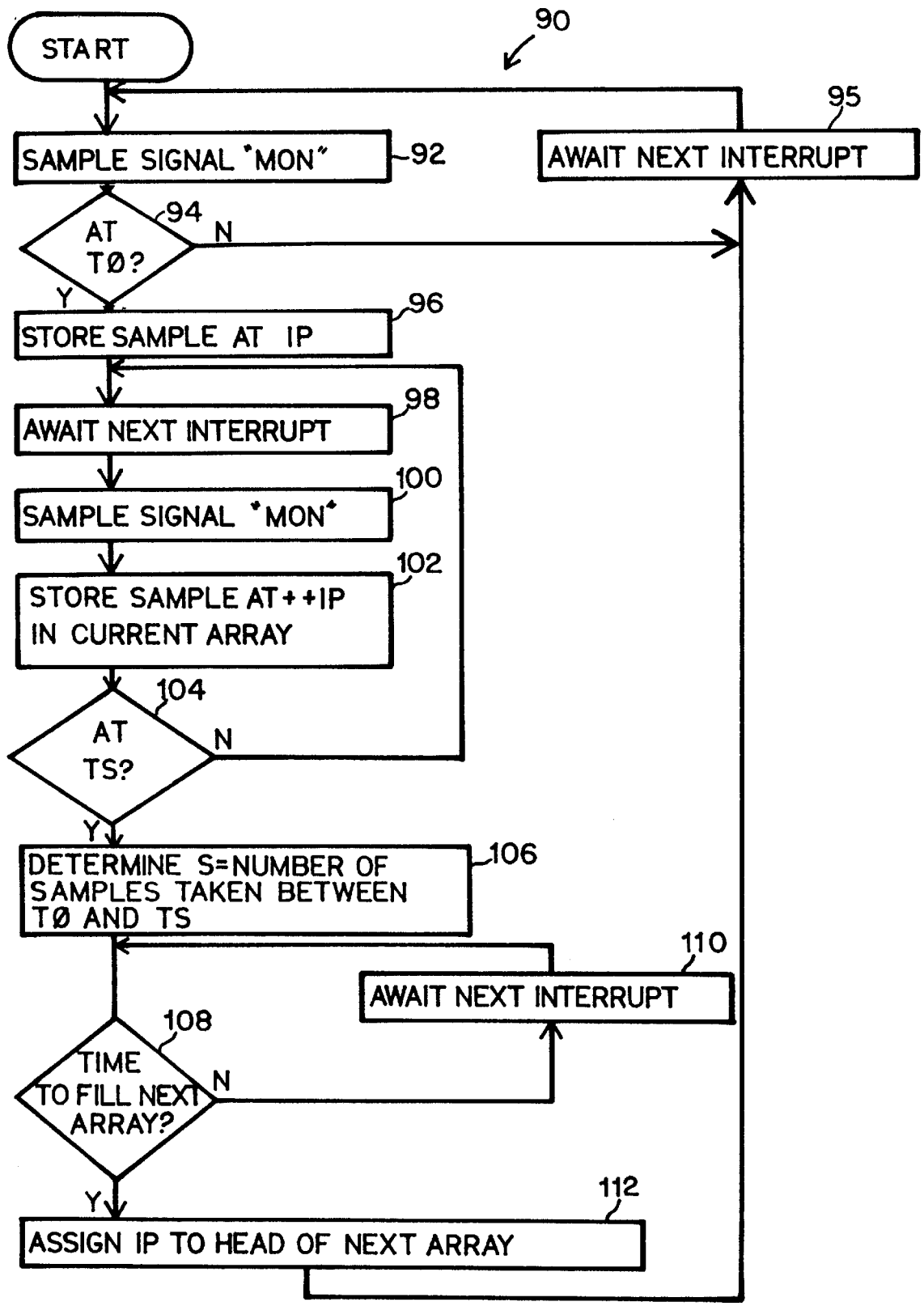
FIG. 5 and FIG. 6 are flow charts of functions performed by microcontroller 76 identified in FIG. 4.
Figure 6:
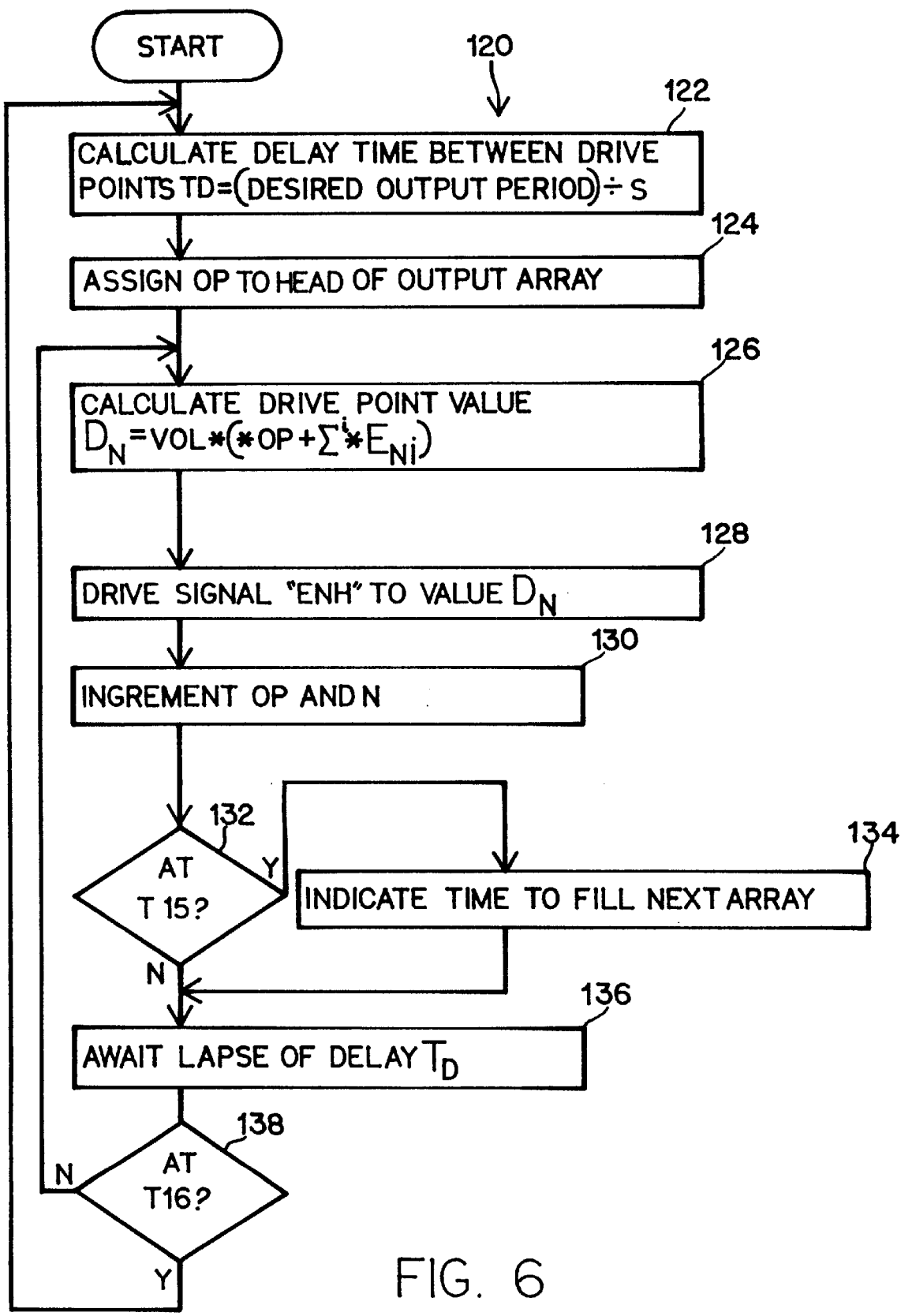

FIGS. 5 and 6 are flow charts of functions performed by microcontroller 76 in FIG. 4. Together, these two flow charts describe a multitasking process having an input service routine 90 and an output service routine 120.

Input service routine 90 is performed in response to a periodic interrupt signal. In an initial condition, the routine is entered at block 92, though other entry points will be discussed. Modification of the entry point is conventionally accomplished, for example, by changing the value of an interrupt vector.

At block 92, a sample of signal MON is taken by ADC 70. Using conventional techniques for zero crossing detection, a determination is made at block 94 whether the sample taken at block 92 corresponds to time T0 in FIG. 3. If not, control passes to block 95 to await the next interrupt. If so, the sample taken at block 92 is stored using an input pointer (IP) that identifies an address in one of two arrays in memory 74. The array pointed to by IP is called the current array; and alternate array is called the next array. After awaiting the next interrupt at block 98, control reenters input service routine 90 at block 100.

Blocks 100 and 102 are within a loop that stores in memory 74 subsequent samples of signal MON as taken at each interrupt by ADC 70. Addresses are calculated by preincrementing the value of input pointer IP. At block 104, another conventional zero crossing test detects whether the sample corresponds to time T5 in FIG. 3. When time T5 is detected, control passes to block 106.

At block 106, a variable S is set to the number of samples taken between times T0 and T5 as detected at blocks 94 and 104. This variable is used at block 122 in FIG. 6 in output service routine 120, discussed below. If the period of signal MON is long, a large number of samples will be taken and stored in the current array. On the other hand, about 64 samples are taken of the shortest expected period for adequate resolution.

At each interrupt following block 106, a test is made of a flag set by output service routine 120 at block 134 in FIG. 6, to be discussed.

When an interrupt occurs after the flag, input pointer IP is assigned a value corresponding to the first address of a next array. This next array thereby becomes the current array. It is then filled with samples of signal MON without disturbing the contents of the array being used by output service routine 120. When output service routine 120 has used all values in an array, that array is available for use by input service routine 90. A minimum of two arrays prevents interference between routines 90 and 120, though embodiments having additional arrays are equivalent.

Output service routine 120 outputs N drive point values spaced in time by delay time $T_D$. Output service routine 120 is implemented as the main program. In an alternate and equivalent embodiment, output service routine 120 is adapted for entry by an interrupt signal that occurs periodically after lapse of the calculated delay time $T_D$.

At block 122, a delay time $T_D$ between drive points as illustrated in FIG. 3 is calculated. The desired output period is divided by the number of samples taken of signal MON by input service routine 90. The desired output period is set in part by settings for a base frequency corresponding to the user's normal tone of voice, in part by control 52 indicating inflection desired by the user, and in part by conventional inflection routines performed by microcontroller 76.

At block 124, an output pointer OP is then set to the first address in the output array corresponding to time T0. The output array is either the current array or an array that was the current array as discussed above with reference to input service routine 90.

Blocks 126 through 138 make up a loop to output N drive point values. At block 126, an Nth drive point value is calculated as a volume, set in part by control 52, multiplied by the sum of several array values. The first array value is pointed to by the current value of output pointer OP. The remaining array values are the Nth values pointed to by several effects array pointers $E_{Ni}$. Each effects array contains values that enhance the remodulated signal. A first effects array may contain, for example, a signature pattern that simulates a unique user's voice as analyzed prior to the onset of disability. Other effects arrays may contain synthesized consonant sounds, discussed below. Selection of effects arrays to use in the summation and weighting of effects array contents are directed in part by control 52.

Superposition is accomplished by adding values for each drive point in block 126. Superposition by the addition of *OP to the summation of effects values is not phase synchronized so the length of each effects array $E_i$ is not critical. The succession of drive points creates the enhanced remodulated signal ENH.

At block 128, the Nth drive point value $D_N$ is used by DAC 78 to slew signal ENH to the next value. The slew rate of DAC 78 is designed to filter high frequency artifacts of digitization. Thus, the number of samples S taken of signal MON corresponds to the number of drive points N. In alternate and equivalent embodiments N is greater than S and additional drive points are calculated by linear or higher order interpolation between consecutive samples of signal MON.

At block 130, output pointer OP and index variable N are incremented. Index variable N is maintained within the bounds of each effects array.

At block 132, a test is made to determine whether the drive point calculated in block 126 corresponds to time T15 in FIG. 3. Time T15 is set to allow sufficient time from time T15 to time T16 for input service routine to sample and store at least one period of signal MON. When the total number of drive points N is equal to the total number of samples S, the test compares the current value of n to a percentage of the total number of drive points, S, for example, 80% of S. When at time T15, a flag is set to indicate that it is time to fill a next array. Input service routine 90 awaits this flag being set at block 108 in FIG. 5.

When not at time T15, control awaits the lapse of delay $T_D$ calculated in block 122. Then, at block 138, a test is made to determine whether all samples have been processed. If not, control passes to the top of the loop at block 126. If so, control passes to block 122 to begin processing samples from another output array.

In a preferred embodiment, circuit 42 performs conventional enhancements for synthesizing speech. For example, in addition to the functions described for routines 90 and 120, circuit 42 responds, in a preferred embodiment, to control 52 for the addition of nonvoiced speech synthesis. Nonvoiced speech includes consonant sounds having minimal tonal quality such as 's', 'sh', 'ch', and etc. These sounds are synthesized to provide drive point values En by an arithmetic combination of table look up values and random number generation. Nonvoiced speech synthesis is combined in such an embodiment with a surrogate voice signal for some voiced consonants, such as 'j', 'v', and etc.

For example, the sound 'v' is synthesized by adding table look up values from memory 74 as a surrogate voice (in place of samples of signal MON) and white noise values from a weighted random number generator. Both the table look up values and the values from the random number generator are scaled for volume and inflection as directed by control 52. Weighting the output of the random number generator helps to distinguish between, for example, 'j' and 'v'.

The foregoing description discusses preferred embodiments of the present invention, which may be changed or modified without departing from the scope of the present invention.

For example, functions performed by digital techniques are equivalently performed by analog techniques (and vice versa) with commensurate modification of the circuitry affected. Functions performed with audible frequencies at subaudible volumes are equivalently performed with subsonic or ultrasonic frequencies and at audible volumes. These and other changes and modifications are intended to be included within the scope of the present invention.

While for the sake of clarity and ease of description, several specific embodiments of the invention have been described; the scope of the invention is intended to be measured by the claims as set forth below. The description is not intended to be exhaustive or to limit the invention to the form disclosed. Other embodiments of the invention will be apparent in light of the disclosure to one of ordinary skill in the art to which the invention applies.

The words and phrases used in the claims are intended to be broadly construed. A "system" refers generally to electrical and mechanical apparatus and includes but is not limited to an electromechanical device, electrostatic device, a magnetic device, an integrated micromachine, a packaged integrated circuit, an unpackaged integrated circuit, a hybrid integrated circuit, a processor, a logic device, a shift register, a memory, a charge-coupled device, combinations thereof, and equivalents.

A "processor" refers generally to apparatus having functions of an analog or digital computer, including for example, a microprocessor, a microcontroller, a digital signal processor, a sequential circuit, a state machine, a standing acoustic wave device, a multiplier, a modulator, a phase locked loop, combinations thereof and equivalents.

A "signal" refers generally to mechanical and/or electromagnetic energy conveying information. When elements are coupled, a signal is conveyed in any manner feasible with regard to the nature of the coupling. For example, if several electrical conductors couple two elements, then the relevant signal comprises the energy on one, some, or all conductors at a given time or time period. When a physical property of a signal has a quantitative measure and the property is used by design to control or communicate information, then the signal is said to be characterized by having a "value." The amplitude may be instantaneous or an average.

Although this invention has been described above with reference to particular means, materials and embodiments, it is to be understood that the invention is not limited to these disclosed particulars, but extends instead to all equivalents within the scope of the following claims.

What is claimed is:

1. A system for monitoring an oral-nasal cavity, the system comprising:

a. a sound source that provides a first subaudible signal in the cavity;

b. a sensor that receives a second signal from the cavity, the second signal being responsive to the first signal and to the cavity, the sensor providing a monitor signal, the monitor signal comprising a first modulation and a first period; and c. a circuit, coupled to the sensor, said circuit comprising a processor, wherein the processor digitizes the monitor signal thereby providing a first sample and a second sample, and determines a third signal in response to the first sample and the second sample, the third signal comprising a second modulation responsive to the first modulation and comprising a second period unequal to the first period.

2. A system for monitoring an oral-nasal cavity, the system comprising:

a. a sound source that provides a first subaudible signal in the cavity;

b. a sensor that receives a second signal from the cavity, the second signal being responsive to the first signal and to the cavity, the sensor providing a monitor signal, the monitor signal comprising a first period; and c. a sampling circuit, coupled to the sensor, that digitizes the monitor signal, thereby providing a first sample and a second sample, and that outputs a third signal responsive to the monitor signal, the third signal comprising a value, wherein the value is responsive to the first sample and to the second sample and comprises an audible frequency and a second period greater than the first period.

3. A system for monitoring an oral-nasal cavity, the system comprising a sampling circuit that receives and digitizes a monitor signal from a provided sensor, the monitor signal comprising a first modulation and a first period, the first modulation being responsive to a first signal from the cavity, the cavity providing the first signal responsive to a second subaudible signal in the cavity, and the second signal responsive to a provided transducer, wherein the circuit is coupled to the transducer so that the second signal is also responsive to the circuit and the circuit provides a third signal in response to the first modulation, the third signal comprising a second period unequal to the first period.

* * * * *